United States Patent [19]
Hart et al.

[11] Patent Number: 5,749,882
[45] Date of Patent: May 12, 1998

[54] APPARATUS FOR DISRUPTING VEIN VALVES

[75] Inventors: Charles C. Hart, Huntington Beach; Eduardo Chi Sing; Mark P. Ashby, both of Laguna Niguel, all of Calif.

[73] Assignee: Applied Medical Resources Corporation, Laguna Hills, Calif.

[21] Appl. No.: 544,860

[22] Filed: Oct. 18, 1995

[51] Int. Cl.⁶ .................................................. A61B 17/32
[52] U.S. Cl. ........................................................ 606/159
[58] Field of Search ......................................... 606/159

[56] References Cited

U.S. PATENT DOCUMENTS

| | | |
|---|---|---|
| 2,655,154 | 10/1953 | Richter . |
| 3,525,339 | 8/1970 | Halligan ............... 606/159 X |
| 3,837,345 | 9/1974 | Majar . |
| 4,273,128 | 6/1981 | Lary ........................ 606/159 |
| 4,493,321 | 1/1985 | Leather . |
| 4,528,982 | 7/1985 | Wellenstam . |
| 4,655,217 | 4/1987 | Reed . |
| 4,739,760 | 4/1988 | Chin et al. . |
| 4,768,508 | 9/1988 | Chin et al. . |
| 4,791,913 | 12/1988 | Maloney . |
| 4,924,882 | 5/1990 | Donovan . |
| 4,952,215 | 8/1990 | Ouriel et al. . |
| 5,026,383 | 6/1991 | Nobles . |
| 5,047,041 | 9/1991 | Samuels . |
| 5,049,154 | 9/1991 | Quadri . |
| 5,061,240 | 10/1991 | Cherian . |
| 5,069,679 | 12/1991 | Taheri . |
| 5,092,872 | 3/1992 | Segalwitz . |
| 5,133,725 | 7/1992 | Quadri . |
| 5,141,491 | 8/1992 | Bowald . |
| 5,152,771 | 10/1992 | Sabbaghian et al. . |
| 5,171,316 | 12/1992 | Mehigan . |
| 5,211,651 | 5/1993 | Reger et al. ............... 606/159 |
| 5,284,478 | 2/1994 | Nobles et al. . |
| 5,514,151 | 5/1996 | Fogarty et al. ............ 606/159 |
| 5,584,842 | 12/1996 | Fogarty et al. ............ 606/159 |

FOREIGN PATENT DOCUMENTS

| | | |
|---|---|---|
| 3717926 | 8/1988 | Germany . |
| WO 8909029 | 10/1989 | WIPO . |

OTHER PUBLICATIONS

"Valvulotome (Detachable Type)", Olympus, Instruction Booklet.

"Leather Retrograde Valvulotome", Baxter (V. Mueller Division), Instruction Booklet, 1988.

"Scanlan International Surgical Instrumentation Catalog", Scanlan Int'l, Inc., St. Paul, MN., 1988, pp. 53, 54.

*Primary Examiner*—Michael H. Thaler
*Attorney, Agent, or Firm*—Richard L. Myers

[57] ABSTRACT

A valvulotome for disrupting valve cusps in the vein of a patient includes a shaft and a cutting member which extends along an axis that defines an axial direction as well as an angular direction. First and second portions of the cutting member define respective cutting edges which extend outwardly of the axis in an angular relationship and an axial relationship with each other. The first and second cutting edges engage and disrupt different cusps of the valve when the shaft is withdrawn axially from the vein. Each of the cutting edges is protected by a proximate shoulder which inhibits the engagement of sidebranches by the associated cutting edge. The cutting member may be formed as a helical blade, a wire or a cylinder and may be provided with a swivel coupling as well as a sheath operable to cover or expose the cutting member.

25 Claims, 6 Drawing Sheets

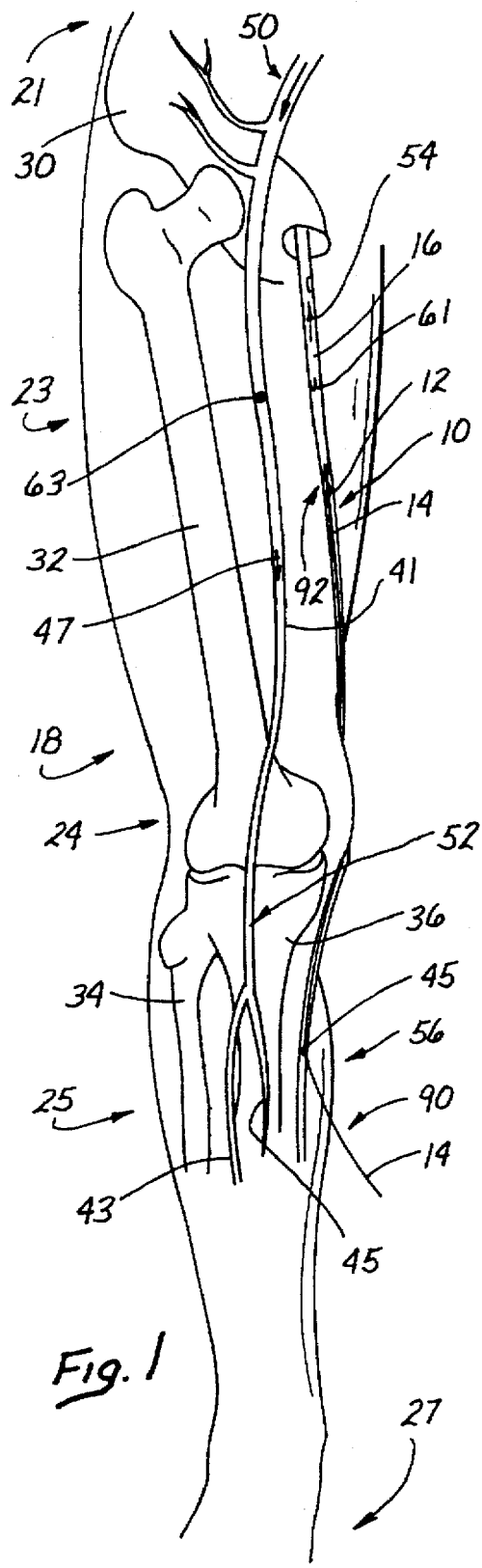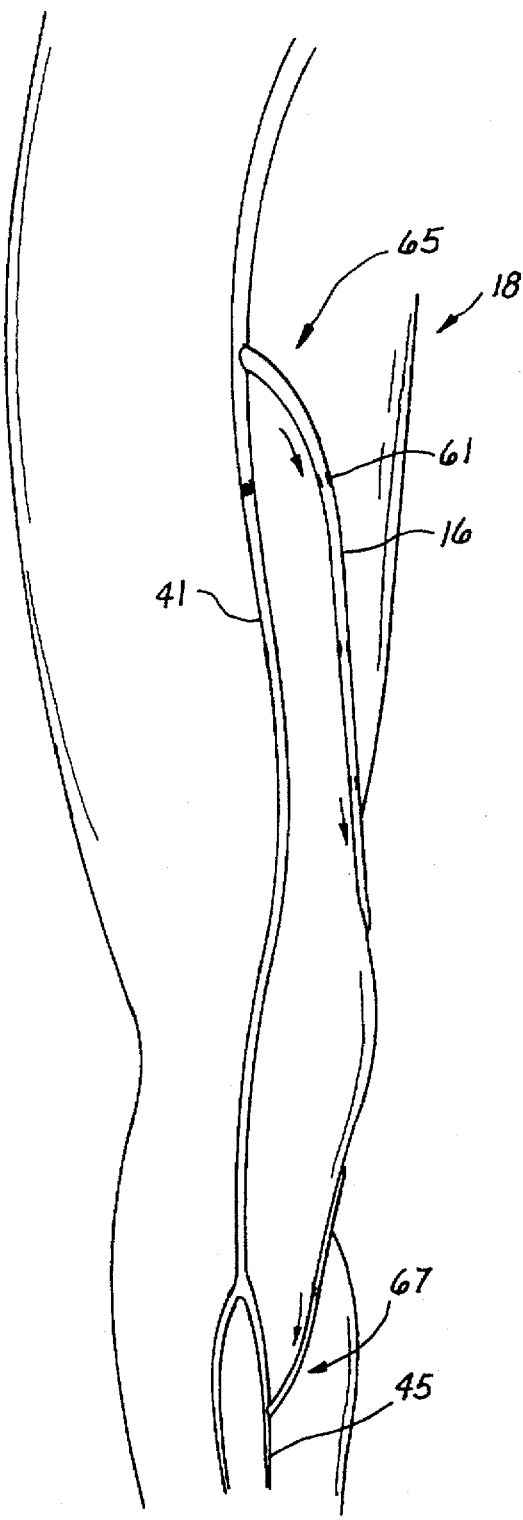

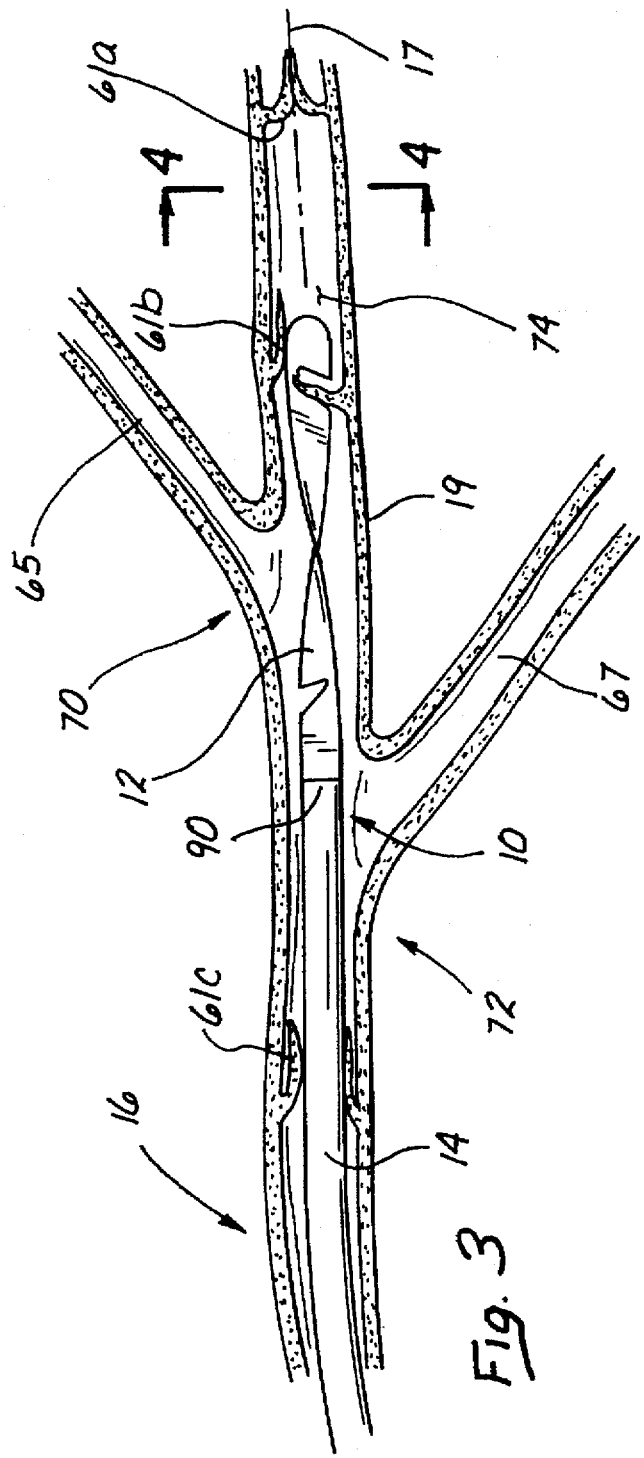
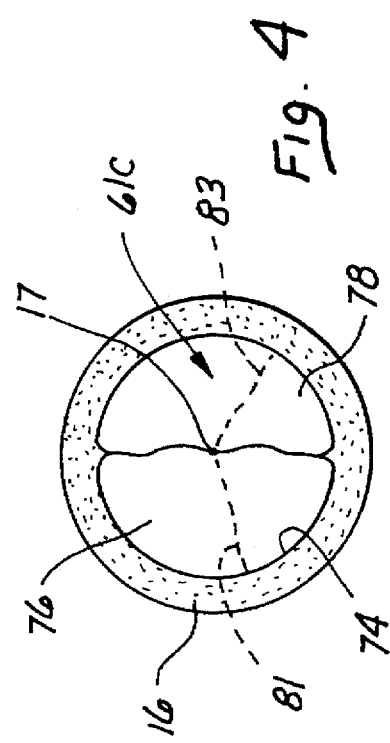

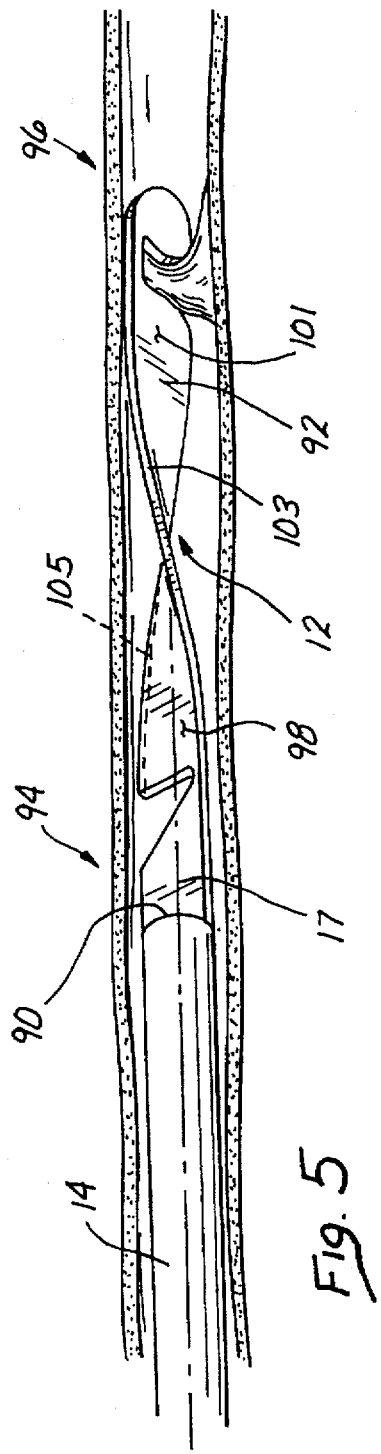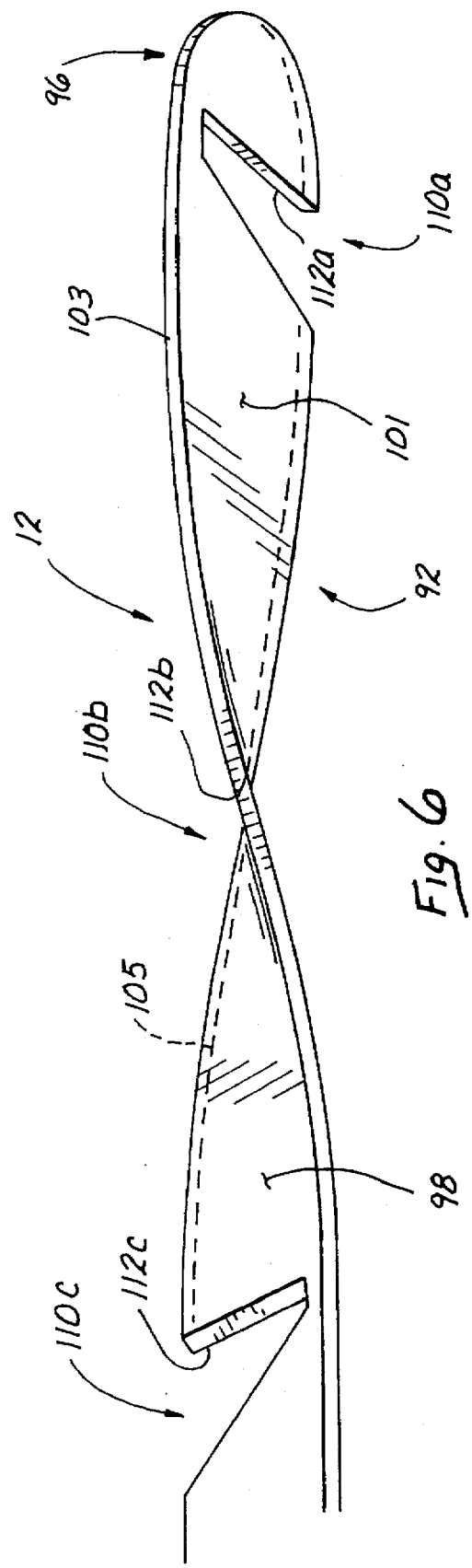

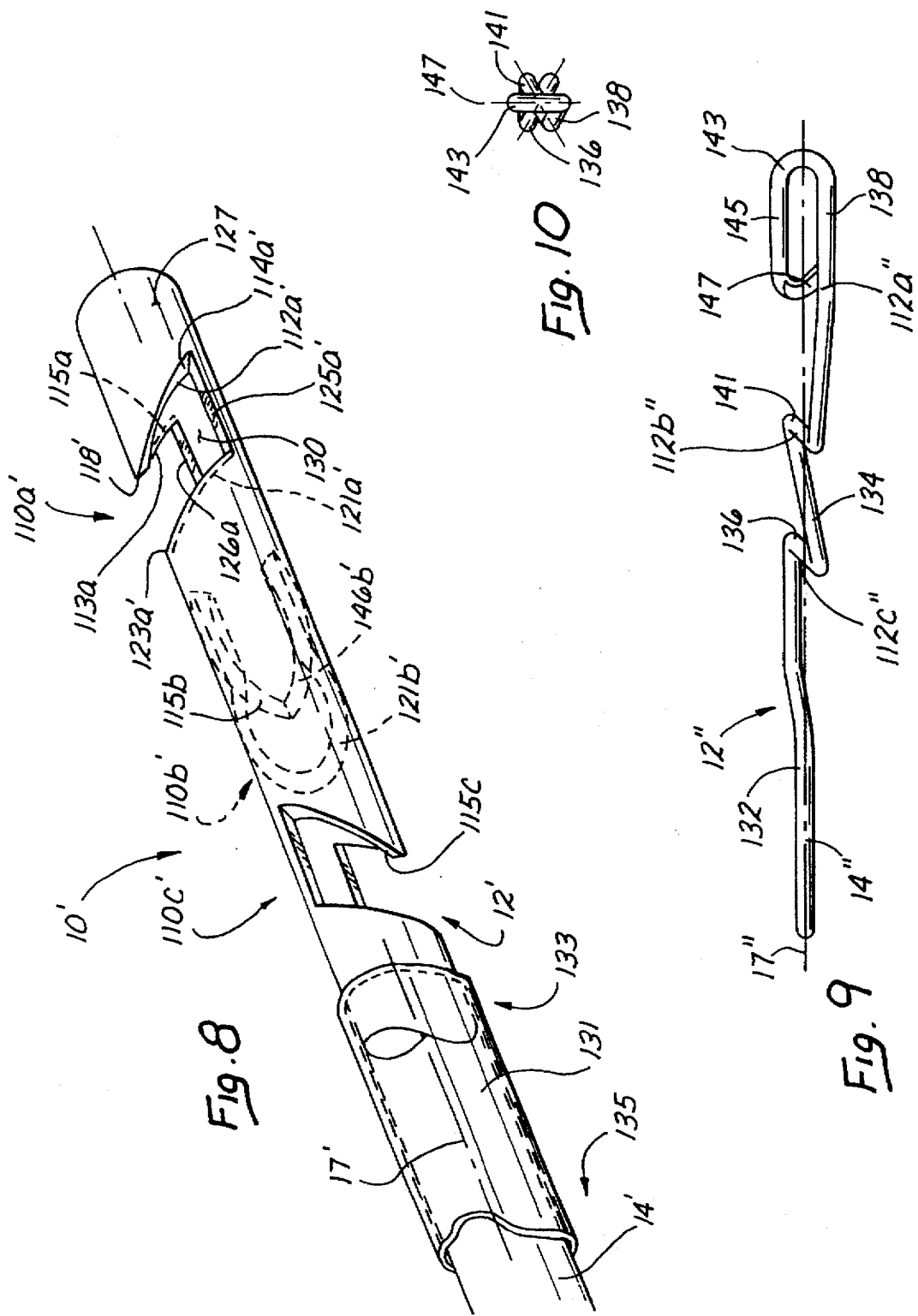

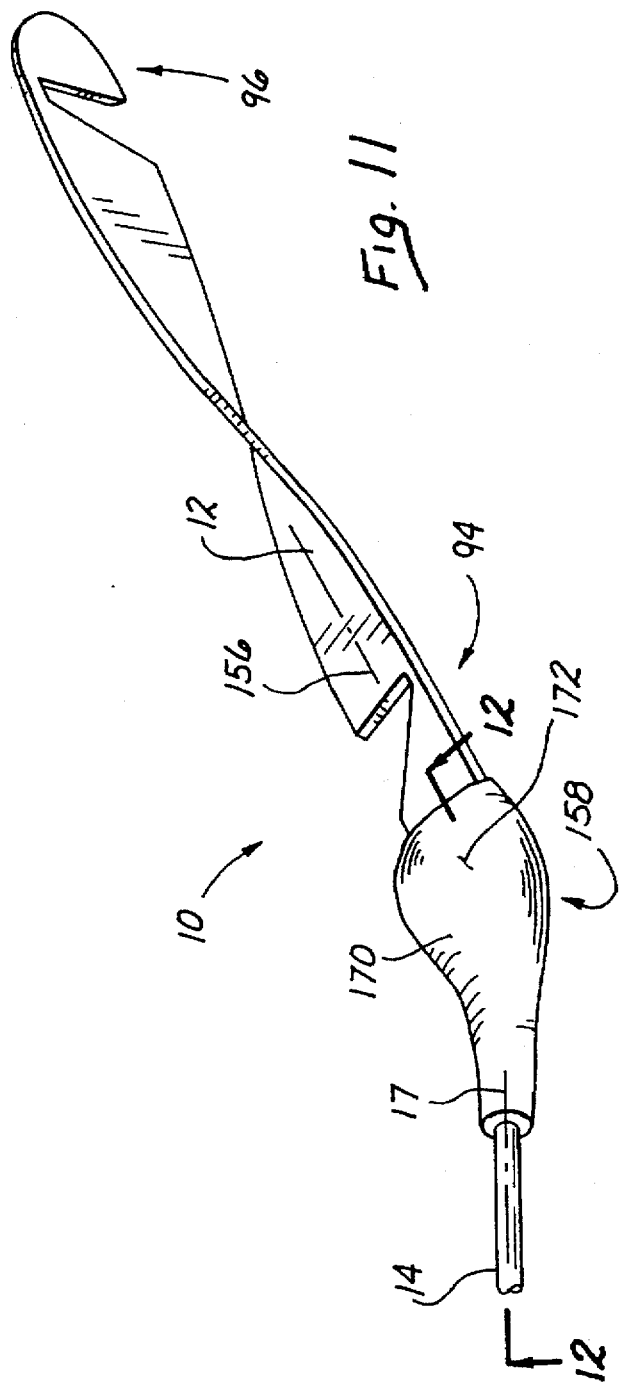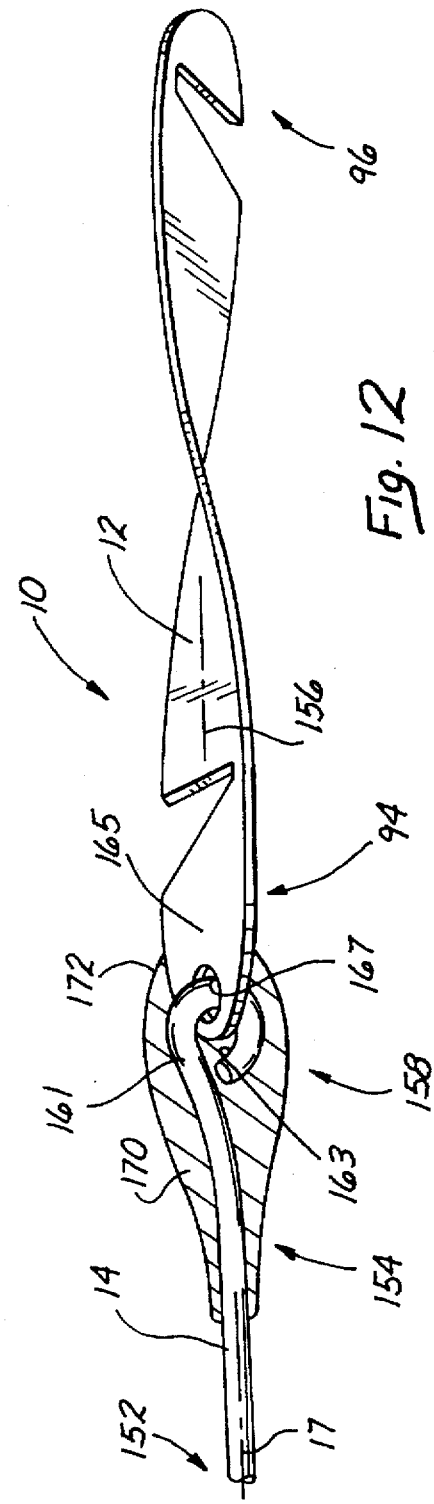

APPARATUS FOR DISRUPTING VEIN VALVES

BACKGROUND OF THE INVENTION

1. Field of the Invention

This invention relates generally to the apparatus and method for disrupting vein valves in a mammal.

2. Discussion of the Prior Art

It is well known that the vascular system is relied on to nourish the cells of the body and to remove waste materials from the cells of the body. More specifically, the arteries of the vascular system convey oxygen and other nutrients to the cells, while the veins of the vascular system return the blood and waste materials from the cells to the lungs, liver, heart and other organs of the body.

Since the flow of blood from the extremities is generally upward, this return flow of blood in the veins must work against the force of gravity. To assist with the return flow, veins commonly include several valves which permit a flow of blood in the upward direction while inhibiting a flow of blood in the downward direction. Thus, the vein valves in their normal state aid in moving the blood in an upward direction against the force of gravity from the extremity to the organs of the body.

The circulation of blood to and from the cells if of particular concern in the extremities of the body, such as the hands and feet, where the cells are located the greatest distance from the organs. When blood is not appropriately circulated, the unnourished cells die sometimes resulting in loss of the associated hand or foot.

In order to avoid amputation, it has long been known that circulation to these extremities may need to be enhanced particularly in old age. When for example, the femoral artery becomes blocked, it is advantageous to bypass this blockage in order to enhance the flow of blood to the lower leg and foot. In a common procedure, the saphenous vein is used for this purpose. Particularly when the blockage occurs in the upper region of the femoral artery, the saphenous vein can be harvested and reversed before attachment to the femoral artery above and below the blockage. This reversal of the vein orients the valves in a direction which facilitates a flow of blood toward rather than away from the extremities.

Particularly for these lower regions, an insitu procedure has evolved where the saphenous vein is left in place but its valves are disrupted in order to enhance a flow of blood in the reverse direction, toward rather than away from the extremity. In this procedure, the proximal end of the vein is attached to the proximal end of the femoral artery, while the distal end of the vein is attached to the distal end of the femoral artery.

It is the description of these valves in the in situ procedure which is of particular interest to the present invention. When the valves are disrupted, the flow of blood in a reversed direction through the vein is enhanced to promote circulation to the extremity.

A vein will typically have several valves along its length each consisting of two and perhaps three cusps sometimes referred to as leaflets. These leaflets form flexible cups which open upwardly. A flow of blood in the upward direction moves the leaflets outwardly permitting the passage of blood. However, the force of blood, typically aided by gravity, in the downward direction fills the cups so that they form seals with each other to inhibit downward flow. The leaflets are typically symmetrical about the axis of the vein. Thus, in a bileaflet valve, the cusps are usually separated by 180°. In a trileaflet valve, the cusps are separated by 120°.

Rendering the valve incompetent should be accomplished with a minimum of operative manipulation. This is important realizing that the inner surface of the vein is lined with endothelial cells which cannot regenerate themselves. Any damage to this endothelial lining can be particularly traumatic to the patient. It has been found that the easiest and least traumatic procedure involves cutting the leaflets radially of the vein axis while they are in their naturally closed position. This cutting of the vein valves is typically accomplished with an instrument referred to as a valvulotome. In the past, these instruments have been provided with a proximally facing cutting surface which has been manipulated to engage each of the leaflets in order to tear the leaflet and render the valve incompetent.

One common valvulotome has the configuration of a hockey stick. Such an instrument must be manipulated into position for each of the leaflets in each of the valves. Accordingly, there is considerable requirement for operative manipulation typically leading to a substantial endothelial damage. Such valvulotome designs also suffer in their tendency to engage side branches of the vein. Where cutting occurs at the junction with side branches, considerable damage can be done to the vein greatly increasing the complexity of the operation and the trauma to the patient. As a consequence, the use of scissors and other valvulotomes of the type discussed has typically been accomplished only under visualization. With this visualization, typically provided by an endoscope, the operator can visualize the process and hopefully avoid damage to the vascular system. Unfortunately, the presence of the endoscope within the vein further enhances the possibility of trauma to the endothelial lining of the vessel. In addition, direct visualization can be time consuming and can add to the blockage which tends to deprive the vein of its blood supply. This even further increases the risk of endothelial damage.

As a result of the aforementioned factors, many of the valvulotomes have been designed to pull the valve leaflet against an anvil or backing so that the cutting element is not exposed to side branches during travel within the vessel. Unfortunately, these devices have been limited in the size of their cut so that generally only a "nip" is made in the cusp. Where this is inadequate, additional passes and cutting of the leaflet is required.

SUMMARY OF THE INVENTION

The foregoing deficiencies noted with respect to the prior valvulotomes and procedures are overcome with the present invention which provides for full radial cutting of each leaflet of each valve in a single, blind pass through the vessel. The valvulotome of the present invention includes a cutting element which can be introduced into the vessel without direct visualization. As a consequence, an endoscope is not required so that the duration of the procedure can be reduced without additional blockage in the vein. Multiple cutting sections are oriented along a plate which is formed with a helical configuration. With this structural orientation, each of the leaflets in this valve will be engaged by at least one of the cutting sections without any axial rotation of the valvulotome. This significantly reduces the operative manipulation necessary for the procedure. By providing multiple cutting sections in the valvulotome, each with its own cutter radially displaced from the cutters in the other sections, each of the leaflets will be cut with a single axial movement of the valvulotome through the vein. The sharp cutting surfaces in each of the cutting sections are oriented to face a shoulder in the cutting section. This shoulder extends outwardly a distance sufficient to inhibit the structure from engaging any irregularities, such as side branches.

In one aspect of the invention, the valvulotome is adapted for disrupting the cusps of the valve in a vein of a patient. The instrument includes a shaft having an elongate configuration which is sized and configured for insertion into the vein along the axis of the vein. A cutting member having an axis extending between a proximal end and a distal end is twisted about the axis. The proximal end of the cutting member is attached to the shaft. First portions of the cutting member define a first cutting edge extending generally outwardly of the axis of the cutting member. Second portions of the cutting member define a second cutting edge which is similar to the first cutting edge. The first portions are angularly displaced from the second portions so that at least one of the first and second portions engage the cusp of the valve regardless of the radial orientation of the valve within the vein.

An additional aspect of the invention includes a valvulotome for disrupting valve cusps in the vein of a patient. A shaft having an elongate configuration is sized and configured for insertion into the vein. A cutting member has an axis extending between a proximal end and a distal end which defines an axial direction extending along the axis and an angular direction extending around the axis. First and second portions of the cutting member define respective first and second cutting edges each of which extends generally outwardly of the axis and faces generally proximally of the cutting member. Third portions of the cutting member define a shoulder disposed in close proximity to the first portions of the cutting member. These third portions define with the first portions of the cutting member a slot which extends proximally with progressive outward positions along the cutting member.

A further aspect of the invention comprises steps of a method for disrupting first and second cusps of a valve in the vein of a patient. The steps include the provision of a valvulotome with a shaft and a cutting member, the shaft having an axis extending between a proximal end and a distal end and the cutting member having a first cutting edge and a second cutting edge. The valvulotome is inserted distally into the vein and beyond the cusps of the valve. When the shaft of the valve is withdrawn proximally. The cutting member is moved through the vein causing the first cutting edge to engage and disrupt the first cusp of the valve and the second cutting edge to engage and disrupt the second cusp of the valve. During the withdrawal step, rotation of the valvulotome is inhibited in order to protect the vein.

In yet a further aspect of the invention, a medical device is adapted for use in a body conduit and includes an operative member having a first axis and a shaft having a second axis, a coupling disposed between the shaft and operative member has swivel characteristics permitting angular movement of the first axis relative to the second axis. A sleeve disposed circumferentially of the coupling between the shaft and operative member has elastomeric characteristics forming a bias which urges the operative member and shaft into an aligned relationship and which permits the angular movement between the operative member and shaft against the bias of the sleeve.

These and other features and advantages of the invention will become more apparent with a discussion of preferred embodiments and best mode of the invention, and reference to the associated drawings.

DESCRIPTION OF THE DRAWINGS

FIG. 1 is a front perspective view of a human leg including an artery with a blockage and a saphenous vein with vein valves;

FIG. 2 is a perspective view of the leg with a saphenous vein retained in situ and the valves disrupted to bypass the blockage in the artery;

FIG. 3 is a side view of the saphenous vein illustrating side branches of the vein in a preferred embodiment of the valvulotome of the present invention;

FIG. 4 is a cross section view of the vein taken along lines 5—5 of FIG. 3;

FIG. 5 is an enlarged view of the vein with the valvulotome being retracted to disrupt a valve in the vein;

FIG. 6 is an enlarged view of a helical blade configuration associated with a preferred embodiment of the valvulotome;

FIG. 8 is a perspective view of a further embodiment of the invention wherein the valvulotome has a cylindrical configuration.

FIG. 9 is a side elevation view of a further embodiment of the valvulotome wherein the cutting member is formed from a wire;

FIG. 10 is an end view of the wire cutting member illustrated in FIG. 9;

FIG. 11 is a side elevation view of a flexible coupling permitting angular movement and displacement of a cutting head and shaft associated with the present invention; and FIG. 12 is a side elevation view partially in section taken along the lines 12—12 of FIG. 11 and illustrating an aligned configuration of the cutting head and shaft.

DESCRIPTION OF PREFERRED EMBODIMENTS AND BEST MODE OF THE INVENTION

Figure 7:
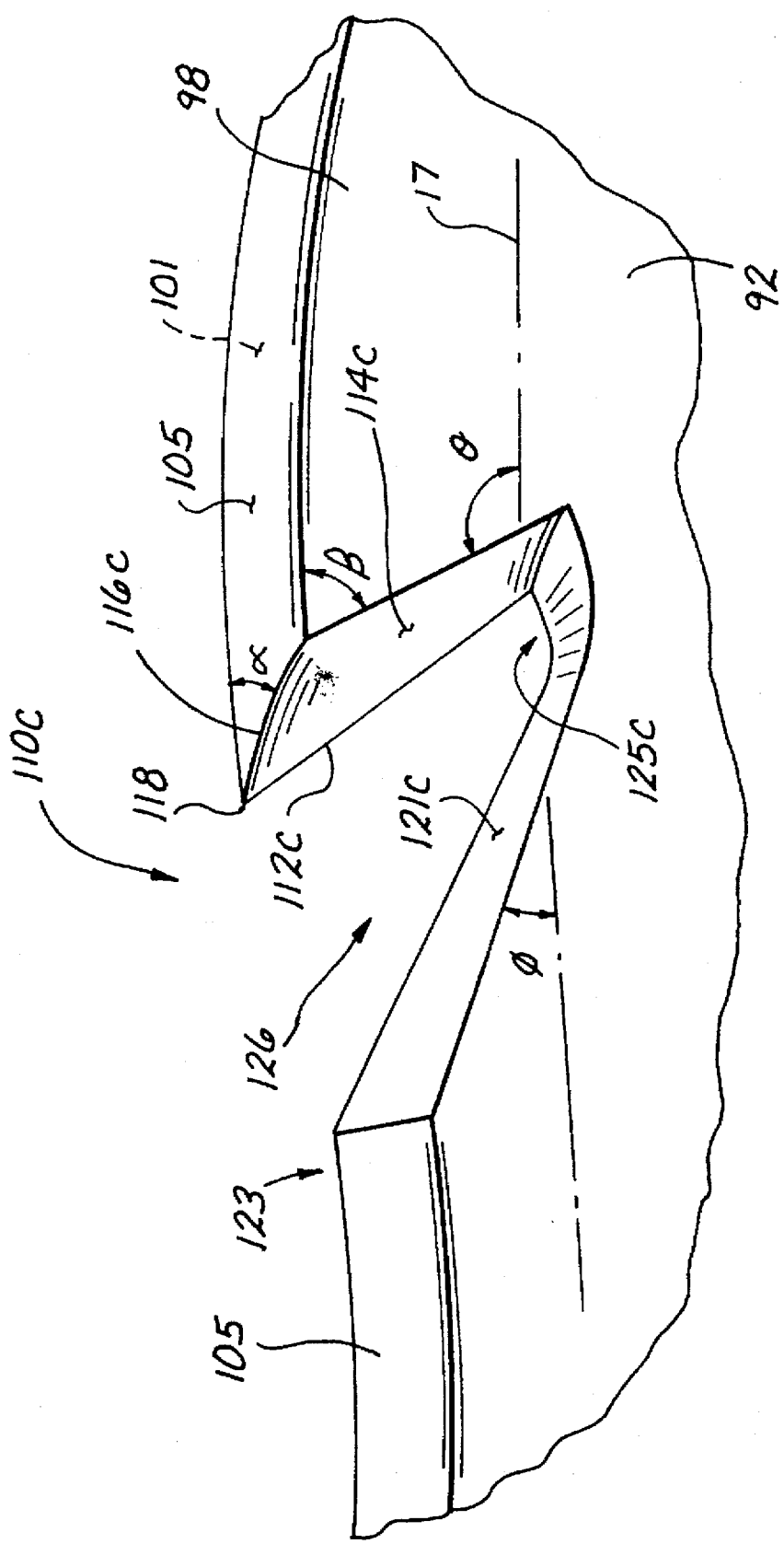
FIG. 7 is an enlarged perspective view of a cutting section associated with one embodiment of the present invention.

A valvulotome is illustrated in FIG. 1 and designated generally by the reference numeral 10. The valvulotome 10 includes a cutting head 12 and a control member or shaft 14. In a preferred embodiment, the shaft 14 is formed from stainless steel or a shaped memory alloy; the cutting head 12 is preferably formed from stainless steel.

In FIG. 1 the valvulotome 10 is illustrated to be operatively disposed in a saphenous vein 16 of a leg 18. the vein 16 has a central axis 17 and a vessel wall 19 which are best illustrated in the enlarged view of FIG. 3. As described in greater detail below, it is the purpose of the valvulotome 10 to prepare the saphenous vein 16 for use as a bypass graft in order to increase the flow of blood to an extremity of the human body. Although the leg 18 is illustrated in FIG. 1, it will be apparent that the valvulotome 10 can be equally effective in preparing other veins such as those occurring in the arms (not shown) to improve circulation for example to the hand.

The leg 18 extends downward from a groin 21 and includes an upper leg or thigh 23, a knee 24, and a lower leg 25 which is connected to a foot 27. The skeletal structure in this region includes a pelvis 30, a femur 32, in the thigh 23, and a tibia 34 and fibula 36 in the lower leg 25.

In the extremities, the circulation system is of greatest interest to the present invention. This system includes arteries which carry blood from the heart (not shown) to the distal regions of the body. In the leg 18, the primary artery is the femoral artery 41 which extends from the area of the groin 21 past the knee 24 into tributaries including the peritoneal artery 43 and the posterior tibial artery 45. It follows that in the femoral artery 41, downstream is toward the extremity, such as the foot 27, and upstream is toward the groin 21. It is the blood flowing in the femoral artery 41 which carries oxygen and other nutrients to the foot 27.

The circulatory system also includes the venous system which carries blood with carbon dioxide and various waste products from the cells at the extremities back to the organs, such as the heart (not shown). In the abdomen, the kidneys remove the waste products from the blood, the lungs oxygenate the blood, and the heart pumps the nutrified blood back into the femoral artery 41.

In the femoral artery 41, blood flows in the direction of an arrow 47 from an upstream end 50 of the groin 21 to a downstream end 52 in the lower leg 25. In the vein 16, the flow is reversed. This flow is in the direction of an arrow 54 from an upstream end 56 to a downstream end 58.

When a person is standing, blood flow in the femoral artery 41 is enhanced by gravitation. However, blood flow in the vein 16 is resisted by gravity. For this reason, the vein 16 commonly includes several valves 61 which facilitate flow toward the downstream end 58 but which inhibit flow toward the upstream end 56. With these valves 61, the flow of blood in the saphenous vein 16 is encouraged against the gravitational force.

The problem being solved by the present invention occurs when the flow of blood to the extremities, such as the hand or foot 27, is insufficient to nourish the cell in those distal regions. This reduced blood flow may result from blockage such as an embolus 63, or arterial sclerosis, a thickening of the vessel walls. In order to improve this blood flow, it is desirable to bypass any restricted portion of the femoral artery with a graft which can carry the nutritive blood parallel with the damaged artery 41. The saphenous vein 16 has been used for this purpose. Turning this vein into an arterial graft removes it from the venous system but other veins can pick up the additional demand for return blood flow.

Preparation of the vein 16 to function as an arterial graph is typically accomplished in an in situ procedure wherein the saphenous vein is retained in its normal orientation in the leg. With this orientation, the valves 61 inhibit the downward flow of blood. Therefore, in accordance with the procedure, the valves 61 are disrupted so that the downward flow, in the direction toward the feet, can be accommodated.

The valvulotome 10 and procedure of the present invention are best illustrated in the enlarged view of FIG. 3 where three of the valves 61 are designated by the reference numerals 61a, 61b and 61c. The vein 16 is further characterized by sidebranches 65 and 67 which communicate with the vein 16 at junctions designated generally by the reference numerals 70 and 72, respectively.

As illustrated in FIG. 3, the valvulotome 10 is being inserted through the vein 16. It is passed through the valve 61c and is in the process of passing through 61b. It has not yet reached valve 61a which is shown in its natural state.

This valve 61a in its natural state is best illustrated in the cross sectional view of FIG. 4. This figure also presents the best view of an endothelial lining 74 which is disposed along the interior surface of the vein 16. This lining 74 is not capable of regenerating itself. As a consequence damage to the lining 74 significantly increases the trauma to the patient.

Also in FIG. 4, the valve 61a is illustrated to have a bileaflet configuration. In other words, it includes two leaflets 76 and 78 which are generally symmetrical but displaced 180° from each other. The leaflet 76 extends from the endothelial lining 74 and extends inwardly across about one-half of the lumen of the vein 16. The leaflet 78 similarly extends from the endothelial lining 74 inwardly toward the leaflet 76. In their natural state, the leaflets 76 and 78 form a seal against each other generally at the axis 17. The purpose of the valvulotome 10 is to cut the leaflets 76 and 78, for example along the dotted lines 81 and 83, respectively. For maximal disruption of the valve 61c, these cuts preferably extend along the entire radius of the leaflets 76, 78 into general proximity with the endothelial lining 74.

The valvulotome 10 is of particular interest to the present invention and includes the shaft 14 and the cutting head 12 as previously discussed. The shaft 14 can be generally any elongate member, having both tension and compression characteristics, which is sufficiently flexible to negotiate the saphenous vein 16. The shaft 14 must have compression characteristics sufficient to push the cutting member 12 through the vein 61. It must also have tension characteristics sufficient to withdraw the cutting member 12 proximally through the vein 61. In a preferred embodiment, the shaft 14 is elongate and cylindrical in configuration. It is formed from either stainless steel or a nickel titanium alloy, and has a diameter of about 0.024–0.028 inches. The shaft 14 is coupled to the cutting member 12 at a junction 90.

It will be noted that the cutting head 12 in the embodiment of FIG. 5 has the configuration of a blade 92 which extends along the axis 17 between a proximal end 94 and a distal end 96. The blade 92 is defined by a pair of generally parallel major surfaces 98 and 101 which are bounded by lateral surfaces 103 and 105 that meet at the distal end 96 as best illustrated in FIG. 6. The blade 92 in this embodiment is twisted into the general configuration of a helix.

Multiple cutting sections 110 are formed along the axis 17 of the blade 92. In the illustrated embodiment, there are three cutting sections designated by the reference numerals 110a, 110b and 110c. These cutting sections 110a–c are similar in size, shape and function in this embodiment. The cutting sections 10a–c are axially spaced relative to each other and, due to the helical configuration of the blade 92, also angularly spaced relative to each other.

Of particular interest to the present invention are a plurality of cutting edges 112a–c each of which is associated with one of the cutting sections 110a–c. For example, the cutting edge 112c is formed by first portions of the blade 92 in the cutting section 110c. Similarly, second portions of the blade 92 form the cutting edge 112b in the cutting section 110b. The cutting edge 112a is formed in the cutting section 110a. It will be noted that in the embodiment of FIG. 6, each of the cutting edges 112a–c faces proximally of the blade 92, and is axially spaced relative to the other cutting edges 112a–c.

Importantly, the cutting edges 112a–c are also angularly spaced relative to each other. In this embodiment, this angular spacing occurs automatically due to the helical configuration of the blade 92. It is this angularly spaced relationship of the cutting edges 112a–c which enables the valvulotome 10 to engage each of the leaflets 76, 78 of the valve 61 without rotation of the shaft 14 or the blade 92 within the vein 16. As a result, all of the leaflets 76, 78 of the valve 61 can be disrupted with a single, non-rotational pass of the valvulotome 10 through the vein 16. This greatly reduces trauma to the patient and offers a high degree of protection for the endothelial layer 74.

Other structural elements associated with the cutting section 110c are discussed with reference to FIG. 7. In this enlarged view it can be seen that the first portions of the blade 92 associated with the cutting edge 112c also define a proximal facing surface 114c which is beveled or otherwise sharpened to form the edge 112c. In the preferred embodiment, the surface 114c is beveled at an angle α, such as 30° relative to the major surfaces 98, 101. With respect to the central axis 17, the surface 114c may have an angle θ. In the preferred embodiment, this angle θ is an obtuse angle such as 120°. This relationship orients the surface 114c at an acute angle B relative to the lateral surface 105. In this embodiment, the angle β is about 48°-50° and is measured at a line of intersection 116c. It will be noted that these angular relationships of the surface 114c relative to the axis 117 and the surfaces 98, 101 and 105, form a point 118c along the cutting edge 112c and the surface 105. Although this point 118 is disposed along the outer edge of the blade 92, it may be blunted in order to inhibit any engagement of the sidebranches 65.

Third portions of the blade 92 define a surface 121c which faces outwardly and distally toward the surface 114c. The surface 121c is generally planar but is angled proximally with progressive positions outwardly of the axis 17. At the lateral surface 105, the surface 121c forms a shoulder 123 which has a preferred orientation relative to the point 118. This orientation is based on both the axial and the radial separation of the shoulder 123 and the point 118. Preferably, the shoulder 123 extends radially from the axis 17 a distance at least as great as the radial displacement of the point 118 from the axis 17. It is also preferable that the shoulder 123 be positioned in sufficient axial proximity to the point 118 that movement of the surface 105 and the shoulder 123 through a vessel will inhibit any cutting contact between the point 118 and the sidebranch 65 (FIG. 3). This axial spacing is preferably within a range of about 0.150-0.175 inches. In a preferred embodiment, the axial spacing of the shoulder 123 relative to the point 118 is about 0.165 inches.

In order to maintain this preferred orientation between the shoulder 123 and the point 118, the surface 121c can be gradually curved into the surface 114c to form a transition surface 125c at the base of the cutting section 110c. The transition surface 125c in a preferred embodiment is disposed on a side of the axis 17 which is opposite the shoulder 123 and the point 118. In other words, the slot formed by the surfaces 114c, 121c and 125c extends across the axis 17. This slot, which is designated by the reference numeral 126 in FIG. 7, extends generally in the direction of its defining surfaces 114c and 121c, that is proximally with progressive outward positions from the axis 17.

As noted above, the shoulder 123 functions to ensure that the point 118 does not engage a sidebranch, such as the sidebranch 65. This same function is served by a different shoulder 124 which is disposed distally of the point 118. This shoulder 124 is defined generally by the major surfaces 98, 101, the lateral surface 105, and the surface 114c. In effect, both the shoulders 123 and 124 function to ensure that cutting occurs only within the cylindrical space defined by the vessel walls. The sidebranches 65 which extend outwardly of that imaginary cylinder cannot be engaged by the point 118 as long as the shoulders 123, 124, and more specifically the lateral surface 105, extend radially at least as far as the point 118.

Each of the shoulders 123, 124 preferably extends axially a distance greater than the diameter of the ostium of a sidebranch. In a normal anatomy, this requirement is generally met if the length of the shoulder 124 along the axis 17 is at least twice as great as the width of the cutting head 12.

There are several advantages associated with the cutting section 110c. With the shoulder 123 extending radially as far as the point 118, it serves as a protective structure which keeps the point 118 from entering any of the sidebranches 65. The shoulder 123 occurs along the surface 105 and does not represent a protrusion or any other area of increased pressure which might damage the endothelial lining 74. While inhibiting any possibility that the cutting section 110c would catch on one of the sidebranches 65, it is nevertheless sized and configured to receive the cusps of a valve such as the valve 61b illustrated in FIG. 3. The depth of the cutting section 110c is relatively deep and preferably extends more than half the distance across the blade 72. This ensures that cutting occurs substantially along the entire radial dimension of the leaflet 76, 78 of the valve 61.

In a preferred embodiment of the invention, the detail disclosed above with reference to the cutting section 110c in FIG. 7 is duplicated in both the cutting section 110a and 111b.

An additional embodiment of the invention is illustrated in the perspective view of FIG. 8. In this embodiment, elements of structure which are similar to those previously disclosed will be designated by the same reference numeral followed by a single prime ('). Thus it can be seen that the embodiment of FIG. 8 includes a cutting head 12' which is molded or otherwise attached to a shaft 14'. Both the cutting head 12' and shaft 14' are disposed along a common axis 17'. This embodiment also includes multiple cutting sections designated by the reference numerals 110a'-c'.

The embodiment of FIG. 8 is similar to that previously discussed in that the cutting sections 110a'-c' are angularly displaced as well as axially displaced relative to each other. It differs from the embodiment of FIGS. 3–7 in the shape of the cutting sections 110a'-c' and also in the configuration of the cutting head 12'. In this case, the cutting head 121 has a cylindrical configuration and can be formed as either a solid cylinder or preferably as a hollow cylinder or tube such as that illustrated in FIG. 8. In either case, the cylinder of the cutting head 12' will have an outer surface 127. In the tubular embodiment, the cylinder of the cutting head 12' will also have an inner surface 130 which defines the cutting edges 112a' and 113, of the cutting head 12'.

Similar to the manner previously described, the cutting section 110a' can include a surface 114a' which is beveled or otherwise sharpened to form a cutting edge 112a'. In this case however the cutting section 110a' also includes a second cutting edge 113a which is formed by a second surface 115a. The configuration of this opposing surface 115a can be better understood with reference to a similar surface 115c which is shown in full view in the cutting section 110c'.

A point 118' is formed at the intersection of the two surfaces 114a' and 115a, with the outer surface 127 of the cutting head 12'. This point 118' can be dulled, blunted or rounded as previously discussed.

Opposing the cutting edges 112a' and 113a is the surface 121a' which is oriented to face the surfaces 114a' and 113a. The surface 121a' can be continuous and planar to facilitate manufacture. A shoulder 123a' is formed at the intersection of the surface 121a' and the outer surface 127 of the cutting head 12'. This shoulder 123a' is not as prominent as that previously described but nevertheless functions to inhibit any snagging of the sidebranches 65 by the point 118'.

If the cylindrical cutting head 12' is provided in a tubular configuration, then the cutting section 110a' will have two transition surfaces 125a' and 126a. These surfaces 125a' and 126a are formed in a single plane in a preferred embodiment.

This particular embodiment offers several advantages including a relatively large outer surface 127 which tends to develop a reduced pressure and hence greater protection for the endothelial lining 74 of the vein 16. The provision of multiple cutting edges 112' and 113 in each of the cutting sections 110a'–c' also provides for greater disruption of the leaflets 76, 78 associated with the valve 61. It may also be easier to grind the cutting sections 110a'–c' when the cutting head 12 is provided in the form of a cylinder rather than a helix.

FIG. 8 illustrates another feature of the invention which may be applicable to each of the embodiments of the valvulotome 10. This feature includes a hollow sheath 131 with a distal portion 133 having an inside diameter greater than the diameter of the cutting head 12. A proximal portion 135 of the sheath 131 extends circumferentially of the shaft 14 to the proximal end of the valvulotome 10. Operation of the proximal portion 135 at the proximal end of the valvulotome 10 moves the distal portion 133 of the sheath 131 between two positions. In the first position, the distal portions 133 of the sheath 131 are disposed circumferentially of the cutting head 12 to cover the cutting edges 112 and thereby prevent cutting. In a second position, the distal portions 133 are disposed circumferentially of the shaft 14 to expose the cutting edges 112 and thereby permit cutting.

A further embodiment of the invention is illustrated in the side view of FIG. 9 and the end view of FIG. 10. In this embodiment, elements of structure which are similar to those previously disclosed will be designated by the same reference numeral followed by a double prime ("). Thus it can be seen that the invention as embodied in FIG. 9 utilizes a cutting head 12" having three cutting edges 112a"–c".

The cutting head 12' includes a first leg 132 which may comprise an extension of the shaft 14". The leg 132 extends generally parallel to the axis 17" and is connected to a second axial leg 134 through a transverse leg 136. Similarly, the second leg 134 is connected to an axial leg 138 through a transverse leg 141. Beyond the third leg 138, the wire forming the cutting head 12' is bent back on itself through an end section 143 to form a return leg 145 which terminates in a third transverse leg 147. It is the transverse legs 136, 141 and 147 which are of particular interest to the present invention since these legs are ground, sharpened or otherwise shaped to form the cutting edges 112c", 112b", and 112a", respectively. With reference to FIG. 9, it can be seen that these cutting edges 112a"–c" are spaced from each other along the axis 17". From the end view of FIG. 10, it can be seen that the transverse legs 147, 141, and 136 are also spaced from each other angularly, in this case by an angle of 120°.

Another feature of the present invention is best illustrated in FIGS. 11 and 12. In these figures, the shaft 14 and the cutting member or head 12 can comprise any of the embodiments previously described. Thus the shaft 14 can be formed from a wire having the axis 17 extending between a proximal end 152 and distal end 154. Cutting head 12 can have an axis 156 extending between the proximal end 94 and distal end 96.

Of particular interest to this embodiment is a flexible coupling designated by the reference numeral 158. This coupling 158 preferably has characteristics which permit angular movement between the axis 17 of the shaft 14, and the axis 156 of the cutting head 12. This angular movement may be desirable as the valvulotome 10 is being drawn through the vein 16 (FIG. 1). Body conduits of this type sometimes form sharp bends and corners which are best negotiated when there is some flexibility between the cutting head 12 and shaft 14.

In the illustrated embodiment, the coupling 158 includes portions 161 at the distal end 154 of the shaft 14 which are bent back on themselves to form a hole 163. Similarly, portions 165 at the proximal end 94 of the cutting head 12 define a hole 167. The portions 161 of the shaft 14 extend through the hole 167 of the cutting head 12, while the portions 165 of the cutting head 12 extend through the hole 163 of the shaft 14. If this embodiment of the coupling 158 were left unrestricted, the resulting interlocking relationship of the portions 161 and 165 would provide a full range of rotation and a full range of displacement of the axis 17 relative to the axis 156. Thus, without regard to orientation of the shaft 14 within the vein 16 (FIG. 1) the coupling 158 would facilitate passage of the valvulotome 10 through substantially any bend or corner in the vein 16.

Notwithstanding these advantageous swivel characteristics, total flexibility of the coupling 158 may not be desired. This is particularly apparent in an embodiment where the cutting head 12 must first be pushed distally into the vein 16 prior to proximal withdrawal from the vein 16. In such an embodiment, it may be desirable to include a coupling cover 170 which is disposed circumferentially of the coupling 158 between the distal end 154 of the shaft 14 and the proximal end 94 of the cutting head 12. In the illustrated embodiment, the cover 170 comprises an overmold which fills all of the interstices of the coupling 158.

This sleeve is preferably formed from an elastomeric material such as silicone, PTFE or polyolefin. This material tends to bias the shaft 14 and cutting head 12 into an aligned configuration wherein the axis 17 is collinear with the axis 156 as illustrated in FIG. 12. This bias and aligned relationship facilitates pushing the valvulotome into the vein 16. While biasing the shaft 14 and cutting head 12 into the aligned configuration, the elastomeric coupling cover 170 also accommodates the desired angular movement and displacement of the cutting head 12 relative to the shaft 14. This movement occurs against the bias provided by the cover 170 so that increasing displacement of the axis 17 relative to the axis 156 is accompanied by increasing resistance from the bias.

In addition to limiting the range of motion permitted by the coupling 158, the cover 170 also provides a tapered outer surface 172 which provides smooth transitions between the shaft 14 and the cutting head 12.

Although the overmold configuration is illustrated in the drawings, the cover 170 can be formed from a heat shrinkable plastic that conforms to the coupling 158. As a further alternative, the cover 170 might be formed as a premolded component which snugly engages the coupling 158.

The coupling cover 170 also functions to provide an enlargement in the vicinity of the coupling 158 which tends to center the axis 17 and/or the axis 158 within the lumen of the vein 16. Such an enlargement could be formed on either side of the coupling 158 and still provide for the centering of the cutting head 12 within the vein 16. This centering feature also contributes to the prevention of encounters between the cutting head 12 and any irregularity, such as a sidebranch 65 or bifurcation, within the lumen of the vein 16.

It will be apparent that the concept of a flexible coupling 158 is broadly applicable to any medical device having an operative member such as the cutting head 12 and an elongate member such as the shaft 14 for pushing and/or pulling the operative member through a body conduit.

From the foregoing description of preferred embodiments, it can be seen that there are many variations on this concept of a valvulotome having multiple cutting sections that are angularly disposed with respect to each other. Although each of the illustrated embodiments shows these cutting sections 110a–c axially disposed, this is not necessarily required by the concept. Nevertheless, where a greater depth of cut is desired, it may be advantageous for the cutting sections 110a–c to be axially displaced.

There may also be some advantage to having cutting sections which are axially displaced but not angularly displaced. In this case, additional cutting of the same leaflet could result in increased disruption of the associated valve.

Of course there are many configurations of the cutting sections 110 which will be capable of disrupting valve leaflets. Generally this will require at least one cutting edge facing proximally to engage the leaflets 76, 78. Where the cutting section 110 is also provided with the shoulder 123, the snagging of adjacent sidebranches can be avoided. This structure opposing the cutting edge 112 can be provided in may different forms each having the required radial and axial separation relative to the point 118.

Given these wide variations, which are all within the scope of this concept, one is cautioned not to restrict the invention to the embodiments which have been specifically disclosed and illustrated, but rather encouraged to determine the scope of the invention only with reference to the following claims.

We claim:

1. A valvulotome for disrupting valve cusps in a vein of a patient, comprising:

a shaft having an elongate configuration and being sized and configured for insertion into the vein;

a cutting member having an axis extending between a proximal end and a distal end, the axis defining an axial direction extending along the axis and an angular direction extending around the axis, the proximal end of the cutting member being attached to the shaft;

first portions of the cutting member defining a first cutting edge extending generally outwardly of the axis of the cutting member; and second portions of the cutting member defining a second cutting edge extending generally outwardly of the axis of the cutting member;

third portions of the cutting member defining a shoulder disposed in close proximity to the first portions of the cutting member, the third portions defining with the first portions a slot which extends proximally with progressive outward positions along the cutting member;

the cutting member having the configuration of a blade extending longitudinally along the axis and being twisted about the axis so that the first portions of the cutting member are axially disposed along and angularly disposed about the axis relative to the second portions of the cutting member; whereby the first cutting edge and the second cutting edge are positioned to engage and disrupt different cusps of the valve when the shaft is withdrawn axially from the vein.

2. The valvulotome recited in claim 1 wherein the cutting member has the configuration of a blade.

3. The valvulotome recited in claim 2 wherein the blade is twisted to form a helix.

4. The valvulotome recited in claim 3 wherein the first portions of the cutting member are spaced axially of the second portions of the cutting member.

5. The valvulotome recited in claim 1 wherein the cutting member is formed from a wire.

6. The valvulotome recited in claim 1 wherein the first cutting edge has a maximum radius in proximity to the first portions of the cutting member and the valvulotome further comprises:

third portions of the cutting member defining a shoulder extending outwardly of the axis to at least the maximum radius of the first cutting edge.

7. The valvulotome recited in claim 6 wherein the third portions of the cutting member defining the shoulder are disposed proximally of the first portions of the cutting member.

8. The valvulotome recited in claim 6 wherein the third portions of the cutting member defining the shoulder are disposed distally of the first portions of the cutting member.

9. The valvulotome recited in claim 1 wherein the cutting member has the configuration of a cylinder.

10. The valvulotome recited in claim 9 wherein the cylinder is a hollow cylinder having an outer surface and an inner surface.

11. The valvulotome recited in claim 1 wherein:

the first portions are angularly displaced from the second portions by an angle of about 120°.

12. A valvulotome for disrupting valve cusps in a vein of a patient, comprising:

a shaft having an elongate configuration and being sized and configured for insertion into the vein;

a cutting member having an axis extending between a proximal end and a distal end, the axis defining an axial direction extending along the axis and an angular direction extending around the axis, the proximal end of the cutting member being attached to the shaft;

first portions of the cutting member defining a first cutting edge extending generally outwardly of the axis of the cutting member and facing generally proximally of the cutting member; and second portions of the cutting member defining a shoulder disposed in close proximity to the first portions of the cutting member defining the cutting edge, the second portions defining with the first portions a slot that extends proximally with progressive outward positions along the cutting member, wherein the cutting member has the configuration of a blade extending longitudinally along the axis and being twisted about the axis.

13. The valvulotome recited in claim 12 wherein the first portions of the cutting member and the second portions of the cutting member define the slot to extend across the axis of the cutting member.

14. The valvulotome recited in claim 12 wherein the slot is further defined by a transition surface, disposed generally at a meeting of the first portions and the second portions, and extending generally longitudinally of the cutting member.

15. The valvulotome recited in claim 14 wherein the transition surface is disposed generally parallel to the axis of the cutting member.

16. The valvulotome recited in claim 12, wherein the cutting member is formed of a cylinder.

17. The valvulotome recited in claim 12, further comprising fourth portions of the cutting member, wherein the third portions and the fourth portions define a second slot which is formed similarly to the slot defined by the first portions and the second portions and which is disposed angularly and axially of the first slot.

18. The valvulotome recited in claim 12 wherein the cutting member is formed from a wire.

19. The valvulotome recited in claim 12 further comprising:
   a sheath movable along the axis between a first position wherein the sheath extends circumferentially of the cutting member and covers the cutting edge to prevent cutting by the cutting member, and a second position wherein the sheath is spaced from the cutting member to expose the cutting edge and permit cutting by the cutting member.

20. A medical device adapted for use in a body conduit, including:
   (a) an operative member having a first axis extending between a proximal end and a distal end of the operative member;
   (b) a shaft having a second axis extending between a proximal end and a distal end of the shaft;
   (c) a coupling disposed between the shaft operative member, the coupling having characteristics permitting angular movement between the first axis of the operative member and the second axis of the shaft, and including:
      (1) first portions of the operative member at the proximal end of the operative member defining a first hole; and
      (2) second portions of the shaft at the distal end of the shaft defining a second hole, the first portions of the operative member extending through the second hole defined by the second portions of the shaft, the second portions of the shaft extending through the first hold defined by the first portions of the operative member, and the operative member and the shaft having an interlocking swivel relationship; and
   (d) a coupling cover disposed circumferentially of the coupling and extending from the distal end of the shaft to the proximal end of the operative member, the cover having elastomeric characteristics forming a bias which urges the operative member and the shaft into an aligned relationship wherein the first axis of the operative member is generally aligned with the second axis of the shaft, and properties permitting the angular movement against the bias.

21. The medical device recited in claim 20 wherein the coupling cover has characteristics for permitting the angular movement of the operative member relative to the shaft with increasing resistance from the bias in response to increasing angular displacement of the first axis of the operative member relative to the second axis of the shaft.

22. The medical device recited in claim 21 wherein the shaft is a wire having compressive characteristics permitting the shaft to be pushed to move the operative member distally through the body conduit, and has tension characteristics permitting the shaft to be pulled to move the operative member proximally through the body conduit.

23. The medical device recited in claim 22 wherein the operative member is a cutting head.

24. The medical device recited in claim 23 wherein:
   the body conduit is a vein having valves with cusps; and
   the cutting head is adapted to disrupt the cusps when the shaft and the cutting head are pulled through the vein.

25. The medical device recited in claim 24 wherein the coupling comprises at least one interstice and the coupling cover comprises an overmold, which fills the at least one interstice of the coupling.

* * * * *

UNITED STATES PATENT AND TRADEMARK OFFICE
CERTIFICATE OF CORRECTION

PATENT NO.  : 5,749,882
DATED       : May 12, 1998
INVENTOR(S) : Hart, et al.

It is certified that error appears in the above-identified patent and that said Letters Patent is hereby corrected as shown below:

In column 13, line 17, after "shaft" please insert --and the--.

In column 13, line 30, please delete "hold" and replace with --hole--.

Signed and Sealed this

First Day of May, 2001

Attest:

NICHOLAS P. GODICI

*Attesting Officer*   Acting Director of the United States Patent and Trademark Office